United States Patent

Buschmann et al.

[11] Patent Number: 5,945,543
[45] Date of Patent: Aug. 31, 1999

[54] PROCESS FOR PRODUCING α-(N,N DIALKYL)-AMINO CARBOXLIC ACID AMIDES

[75] Inventors: Ernst Buschmann, Ludwigshafen; Thomas Zierke, Böhl-Iggelheim, both of Germany

[73] Assignee: BASF Aktiengesellschaft, Ludwigshafen, Germany

[21] Appl. No.: 08/983,287

[22] PCT Filed: Jul. 12, 1996

[86] PCT No.: PCT/EP96/03075

§ 371 Date: Jan. 20, 1998

§ 102(e) Date: Jan. 20, 1998

[87] PCT Pub. No.: WO97/05096

PCT Pub. Date: Feb. 13, 1997

[30] Foreign Application Priority Data

Jul. 28, 1995 [DE] Germany .................. 195 27 574

[51] Int. Cl.⁶ .................. C07C 231/02; C07K 1/08; C07K 1/06
[52] U.S. Cl. .................. 548/524; 530/300; 548/538; 549/172; 560/27; 564/138; 564/139; 564/140; 564/141
[58] Field of Search .................. 548/538, 524; 564/140, 138, 139, 141; 560/27; 549/172; 530/300

[56] References Cited

U.S. PATENT DOCUMENTS

| 1,972,142 | 9/1934 | Goldstein | 564/138 X |
| 4,331,592 | 5/1982 | Wissmann et al. | 560/27 X |
| 4,426,325 | 1/1984 | Wissmann et al. | 564/138 X |
| 4,912,127 | 3/1990 | Henning et al. | 514/422 |

FOREIGN PATENT DOCUMENTS

| 14 834 | 9/1980 | European Pat. Off. |
| 0156280 | 12/1984 | European Pat. Off. |
| 93/23424 | 11/1993 | WIPO |

OTHER PUBLICATIONS

Tetrahedron, vol. 50, No. 18, 5345–5360 1994 Roux et al.
J. Am. Chem. Soc. 1991, 113, 6692–6693 Petit et al.
Liebig, Ann. Chem. Schmidt et al. 1254–1257 (1985).
Tetrahedron, vol. 49, No. 41, Oct. 1993 Petit et al II.

*Primary Examiner*—Floyd D. Higel
*Attorney, Agent, or Firm*—Keil & Weinkauf

[57] ABSTRACT

A process for preparing α-(N,N-dialkylamino) carboxamides of the formula I

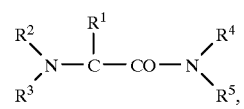

where the substituents have the stated meanings, comprises reacting the corresponding free acids with primary or secondary amines in the presence of anhydrides of an alkanephosphonic acid.

5 Claims, No Drawings

PROCESS FOR PRODUCING α-(N,N DIALKYL)-AMINO CARBOXLIC ACID AMIDES

This is a 371 of PCT/EP96/03075 filed Jul. 12, 1996.

The invention relates to a novel process for the racemization-free linkage of α-(N,N-dialkyl)-amino acids with amines to give the corresponding carboxamides.

There is interest in α-(N,N-dialkyl)-amino acids of the formula II

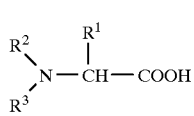

II as building blocks for the synthesis of numerous natural substances with an interesting profile of pharmacological actions and for active substances structurally derived from these substances (enkephalins: U. Schmidt et al.; Liebigs Ann. Chem. (1985) 1254–1262, dolastatins: G. R. Pettit et al.; Tetrahedron 49 (41) 9151–9170, WO 93/23 424). Thus, for example, the antineoplastic active substance dolastatin 10 is prepared from N,N-dimethylvaline (IIa) and a tetrapeptide:

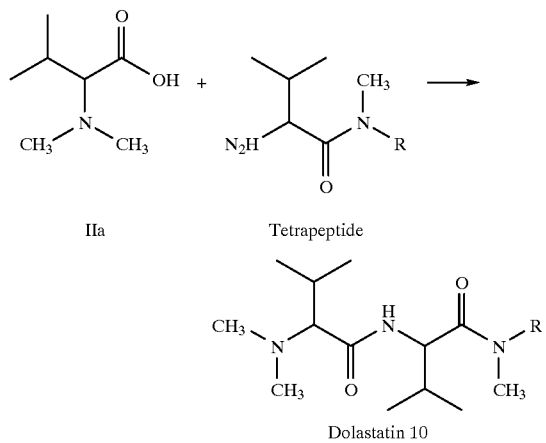

IIa            Tetrapeptide

Dolastatin 10

The linkage of an N,N-dialkylamino acid such as IIa with peptides is difficult and, in the case of dolastatin 10, gave a yield of only 53% (J. Poncet et al. Tetrahedron 50, (1994) 5345–5360). This poor result, which leads to loss of a large portion of the valuable tetrapeptide in the dolastatin synthesis, is not surprising according to U. Schmidt et al. (Liebigs Ann. (1985) 1254–1262).

U. Schmidt also investigated the linkage of N,N-dimethylamino acids in connection with the synthesis of enkephalins. In this connection, only three methods proved to be useful for activating these amino acids:

1. Activation of the N,N-dimethylamino acid by conversion into the pentafluorophenyl esters:

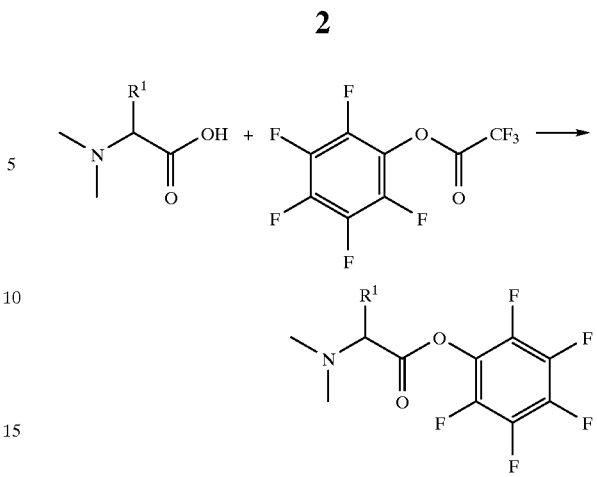

This method is used, for example, by G. R. Pettit et al. (J. Am. Chem. Soc. 113 (1991) 6992–6993) for synthesizing dolastatin 15. The starting compound required for this multistage process is pentafluorophenol, a costly reagent which is not available in sufficient quantity for industrial syntheses. Its use moreover leads to fluorine-containing waste which can be disposed of only with difficulty and possibly with formation of dioxins.

2. As an alternative, U. Schmidt recommends activation with 3-cyano-4,6-dimethyl-2-pyridinethiol:

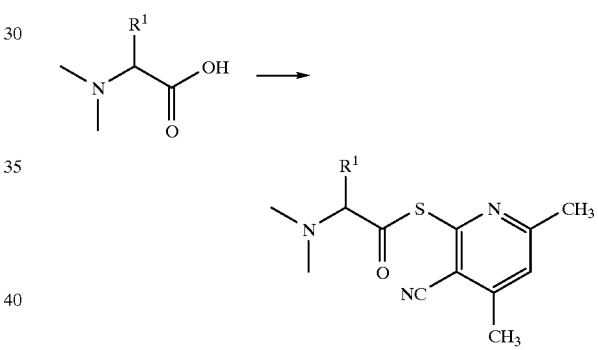

However, the cyanopyridine is not commercially available and must be prepared in a multistage process.

3. A third alternative is activation of the dimethylamino acid with diethyl phosphocyanidate (=DEPC) (G.R. Pettit, Tetrahedron 50 (1994), 42, 12097–12108). This reagent is also not commercially available in the amounts necessary for industrial synthesis. An additional multistage process is necessary. Highly toxic cyanide-containing solutions must be used in the preparation and reaction of DEPC.

There is thus a pressing need for processes which make simple linkage of N,N-dimethylamino acids possible.

However, there is interest not only in peptide linkage of N,N-di-methylamino acids but also in peptide couplings with N-benzyl-N-methylamino acids. In this case, the benzyl radical acts as protective group which can easily be eliminated by hydrogenolysis.

Although N-benzyl-N-methylamino acids can easily be prepared as peptide building blocks, they are little used because to date there have been no methods which can be used for racemization-free linkage of these amino acids.

This is why peptides which are partly composed of N-methylamino acids (eg. cyclosporins, dolastatins) are prepared exclusively using N-acyl-N-methylamino acids (acyl=butoxycarbonyl (BOC), benzyloxycarbonyl (Z)) which, although more difficult to prepare than N-benzyl-N-methylamino acids, are less prone to racemization on linkage (example: Dolestatin 15 synthesis by G. R. Pettit, J. Am. Chem. Soc. 113 (1991) 6692–6693).

A suitable coupling reagent for using N-benzyl-N-methylamino acids would therefore also be desirable.

Linkage of carboxylic acids with amines in the presence of anhydrides of alkanephosphonic acids to give the corresponding amides is a familiar process (EP 14 834) which can also be used to prepare peptides (EP 156 280). n-Propanephosphonic anhydride (PPA) is preferably used for this purpose. However, the utilizability of this reagent has been shown only for N-acylamino acids which are not alkylated on the nitrogen.

Numerous coupling reagents are available for such reactions. The utilizability of anhydrides of alkanephosphonic acids for linking N,N-dialkylamino acids of the formula I has not hitherto been investigated.

It was therefore surprising in the context of the problems indicated above that anhydrides of alkanephosphonic acids are very suitable coupling reagents for linking α-(N,N-dialkyl)-amino acids.

The invention relates to a process for preparing α-(N,N-dialkylamino) carboxamides of the formula I

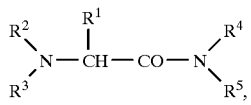

where $R^1$ is $C_{1-6}$-alkyl, $C_{3-7}$-cycloalkyl, phenyl, benzyl, $(CH_2)_3NH(C=NH)NH_2$, $CH_2CONH_2$, $CH_2CO_2H$, $CH_2SH$, $(CH_2)_2CONH_2$, $(CH_2)_2CO_2H$, imidazolyl-5-methylene, $(CH_2)_4NH_2$, $(CH_2)_2SCH_3$, $CH_2OH$, $CH(OH)CH_3$ or indolyl-β-methylene, where reactive groups are, if required, provided with protective groups, $R^2$ is $C_{1-6}$-alkyl or unsubstituted or substituted benzyl, $R^3$ is $C_{1-6}$-alkyl or unsubstituted or substituted benzyl, where $R^1$ and $R^3$ can be linked together, $R^4$ and $R^5$ are, independently of one another, hydrogen, $C_{1-6}$-alkyl, $C_{3-7}$-cycloalkyl, phenyl (which can be substituted by 1, 2 or 3 fluorine, chlorine or bromine atoms or $C_{1-5}$-alkyl, $C_{1-5}$-alkoxy or $CF_3$ groups), an aromatic heterocycle (which can be substituted by 1, 2 or 3 fluorine, chlorine or bromine atoms or $C_{1-5}$-alkyl, $C_{1-5}$-alkoxy or $CF_3$ groups) or benzyl (which can be substituted by 1, 2 or 3 fluorine, chlorine or bromine atoms or $C_{1-5}$-alkyl, $C_{1-5}$-alkoxy or $CF_3$ groups), where $R^4$ and $R^5$ can additionally be linked together, and where $NR^4R^5$ can also be an amino acid residue or peptide residue, the carboxyl group and other functional groups possibly being blocked with protective groups, which comprises reacting the corresponding free acids with primary or secondary amines in the presence of anhydrides of an alkanephosphonic acid.

Specific mention may be made in particular of the following primary and secondary amines

amines such as ammonia, methylamine, ethylamine, propylamine, butylamine, isobutylamine, benzylamine, cyclohexylamine, dimethylamine, diethylamine, benzylmethylamine, dibenzylamine, pyrrolidone, hydroxy- and methylpyrrolidines, piperidine, hydroxy and methylpiperidines, aniline, N-methylaniline, morpholine, alkylmorpholines, aminopyridine;

amino acid derivatives such as esters and amides of alanine, N-methylalanine, glycine, N-methylglycine, isoleucine, N-methylisoleucine, methionine, N-methylmethionine, phenylglycin, N-methylphenylglycine, phenylalanine, N-methylphenylalanine alanine, proline, tryptophan, N-methyltryptophan, valine, N-methylvaline, β-alanine, N-methyl-β-alanine;

peptides such as Val-MeVal-OMe, MeVal-Val-OMe, Pro-Val-OMe, Pro-Val-NH$_2$, Pro-Val-NHBz, Val-MeVal-Val-Pro-OMe, Val-MeVal-Val-Pro-NH$_2$, Val-MeVal, Val-Pro-NHBz, Val-MeVal-Val-Pro-NHiProp, Val-MeVal-Pro-ProNH$_2$, Val-MeVal-Pro-Pro-NHBz, Val-MeVal-Pro-Pro-NHiProp.

Particularly suitable for $R^1$ as $C_{1-6}$-alkyl or $C_{3-7}$-cycloalkyl are: methyl, isopropyl, isobutyl, 1-methylpropyl, cyclopropyl and cyclohexyl.

The $C_{1-6}$-alkyl groups specifically mentioned for $R^1$ are also preferred for $R^2$, $R^3$, $R^4$ and $R^5$. Cycloalkyl groups which may be particularly mentioned for $R^4$ and $R^5$ are cyclopropyl and cyclohexyl.

Suitable and preferred aromatic heterocycles for $R^4$ and $R^5$ are thiazole, thiophene and pyridine radicals.

$R^4$ and $R^5$ can also be connected together by the following bridges so that $R^4R^5$ is then $(CH_2)_4$, $(CH_2)_5$, $CH_2CH_2OCH_2CH_2$ or $(CH_2)_6$.

$R^1$ and $R^2$ can be linked together to form, where appropriate, $C_1$–$C_4$-alkyl-substituted pyrrolidines and piperidines.

Besides an alkyl group, $R^2$ can also be an unsubstituted or substituted benzyl radical. Suitable substituents are $C_1$–$C_4$-alkyl, $C_1$–$C_4$-alkoxy, nitro, $CF_3$, Cl, F and Br.

The process according to the invention is thus suitable both for preparing amides of the N,N-dialkylamino acids I and particularly for preparing peptides.

The reaction is carried out at from −10° C. to +40° C., preferably from −5° C. to room temperature. Suitable coupling reagents are the anhydrides of the straight-chain or branched, or cyclic, alkanephosphonic acids with chain lengths of from 1 to 8 carbon atoms, preferably propanephosphonic anhydride (PPA). Other examples which may be mentioned are methanephosphonic anhydride, ethanephosphonic anhydride and butanephosphonic anhydride.

The alkanephosphonic anhydrides can be prepared in a conventional manner as described, for example, in Houben-Weyl, Meth. d. Org. Chem. (1963), Vol. XII/1, page 612.

Particularly pure alkanephosphonic anhydrides are expediently used to prepare peptides. Anhydrides of this type can be obtained by reacting pure alkanephosphonic dichlorides with 1 mole of water and subsequently removing the hydrogen chloride which still remains in the product under reduced pressure.

The process of German Patent Application 2 811 628 is preferred for preparing these anhydrides. This entails pure alkanephosphonic acids being converted into the anhydrides by thermal elimination of water. Subsequent purification by vacuum distillation may be expedient. The reaction is best carried out in neutral or weakly alkaline medium.

The condensation reaction is expediently carried out in a buffered medium, which can take place by adding aliphatic and cycloaliphatic tertiary bases such as N-methylmorpholine, N-ethylmorpholine, and trialkylamines with up to 6 carbon atoms per alkyl radical. Triethylamine and diisopropylethylamine have proved particularly useful. Suitable solvents are dimethyl sulfoxide, DMF, DMA, N-methylpyrrolidone, chloroform, methylene chloride, THF, dioxane and methyl acetate.

The starting materials used to prepare peptides are, besides the N,N-dialkylamino acid or the N-benzyl-N-alkylamino acid and the anhydride of the alkanephosphonic acid, an amino acid or a peptide with a blocked carboxyl group. The carboxyl group can be protected using all protective groups customary in peptide synthesis.

The alkanephosphonic anhydrides are preferably employed in excess (2 to 2.5 mol of alkanephosphonic anhydride per mole of amide linkage to be produced).

The following examples illustrate the process according to the invention.

EXAMPLE 1

Me$_2$Val-Val-MeVal-Pro-Pro-NHBzxHCl 42.4 g of a 50% strength solution of n-propanephosphonic anhydride in ethyl acetate were added dropwise over the course of 20 min to a solution of 8.7 g of L-N,N-dimethylvaline, 27.4 g of Val-MeVal-Pro-Pro-NHBzxHCl and 21.6 g of triethylamine in 100 ml of CH$_2$Cl$_2$ at 0 to 65° C. The mixture was stirred in the cold for 1 h and at room temperature overnight. The organic phase was washed with 50 ml of water and concentrated. The residue was dissolved in 50 ml of isopropanol and acidified with 10 ml of 30% strength isopropanolic HCl. Seeding, addition of 150 ml of methyl tert-butyl ether at 60° C., stirring overnight, filtering with suction, washing with isopropanol and drying resulted in 29.9 g (88.3%) of Me$_2$Val-Val-MeVal-Pro-Pro-NHBzx HCl, purity by HPLC percentage area: 99.8% (no epimer detectable).

EXAMPLE 2

Me$_2$Val-Val-MeVal-Pro-Pro-NHBzxHCl 84.8 g of a 50% strength solution of n-propanephosphonic anhydride in ethyl acetate were added dropwise over the course of 45 min to a solution of 21.6 g of dimethylvaline, 54.8 g of Val-MeVal-Pro-Pro-NHBzxHCl and 54 g of diisopropylethylamine in 100 ml of CH$_2$Cl$_2$ at −75° C. The mixture was stirred in the cold for 1 h and at room temperature overnight. The organic phase was washed with 200 ml of saturated NaCl solution and 100 ml of 10% strength NaOH and concentrated. The residue was dissolved in 350 ml of 2-butanol. 25 ml of saturated isopropanolic HCl solution and 200 ml of MTBE were added and, after stirring overnight, the product was filtered off with suction and dried under reduced pressure to result in 61.4 g (90.5%) of product, purity by HPLC percentage area: 99.8% (no epimer detectable).

EXAMPLE 3

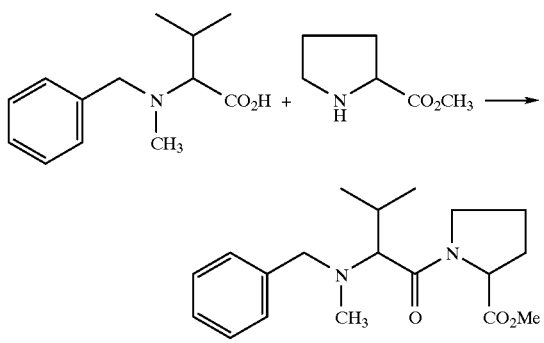

120 g of diisopropylethylamine were added to a solution of 50 g of N-benzyl-N-methylvaline in CH$_2$Cl$_2$. 37.7 g of proline methyl ester hydrochloride and 176.8 g of 50% strength solution of propanephosphonic anhydride in ethyl acetate were added at −55 to 5° C. The mixture was stirred in the cold for 1 h and at room temperature overnight. The organic phase was washed with 400 ml of water, 200 ml of 1 N NaOH and twice with water, dried over Na$_2$SO$_4$ and concentrated. 49.6 g (65.4%) of product were obtained, purity by HPLC percentage area: 93.7%. The content of other diastereomers was below 1%.

EXAMPLE 4

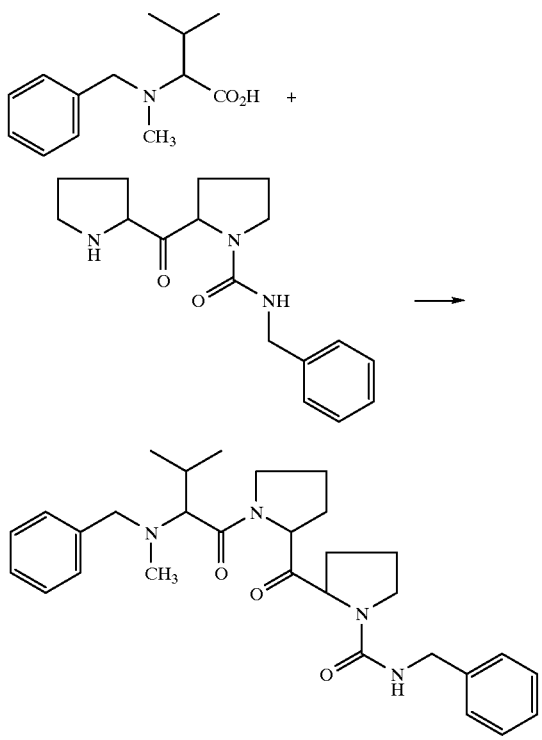

9.9 g of Pro-Pro-NHBzxHCl and 24.3 g of a 50% strength solution of n-propanephosphonic anhydride in ethyl acetate were added to a solution of 6.5 g of N-benzyl-N-methylvaline and 16.3 g of diisopropylethylamine in methylene chloride at −55° C. to 5° C. The mixture was stirred in the cold for 1 h and at room temperature overnight, and the organic phase was washed with water, 1 N NaOH and water, dried over Na$_2$SO$_4$ and concentrated. 14.4 g (93.4%)

of product remained, purity by HPLC percentage area: 96.1%. The content of other diastereomers was below 1%.

We claim:

1. A process for preparing an α-(N,N-dialkylamino) carboxamide of the formula I

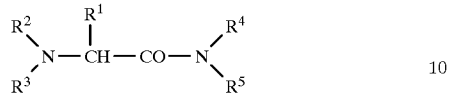
(I)

where

- $R^1$ is $C_{1-6}$-alkyl, $C_{3-7}$-cycloalkyl, phenyl, benzyl, $(CH_2)_3NH(C=NH)NH_2$, $CH_2CONH_2$, $CH_2CO_2H$, $CH_2SH$, $(CH_2)_2CHNH_2$, $(CH_2)_2CO_2H$, imidazolinyl-5-methylene, $(CH_2)_4NH_2$, $(CH_2)_2SCH_3$, $CH_2OH$, $CH(OH)CH_3$ or indolyl-β-methylene, wherein any functional group capable of participating in the process is unprotected or protected by a protective group,
- $R^2$ is $C_{1-6}$-alkyl or unsubstituted or substituted benzyl,
- $R^3$ is $C_{1-6}$-alkyl or unsubstituted or substituted benzyl, or
- $R^1$ and $R^3$ taken together with the N atom to which they are bonded, form a pyrrolidine or piperidine ring, which ring is unsubstituted or substituted by $C_{1-4}$-alkyl groups,
- $R^4$ and $R^5$ are, independently of one another, hydrogen, $C_{1-6}$-alkyl, $C_{3-7}$-cycloalkyl, phenyl, which is unsubstituted or substituted by 1, 2 or 3 fluorine, chlorine or bromine atoms or $C_{1-5}$-alkyl, $C_{1-5}$-alkoxy or $CF_3$ groups, or an aromatic heterocycle, which is unsubstituted or substituted by 1, 2 or 3 fluorine, chlorine or bromine atoms or $C_{1-5}$-alkyl, $C_{1-5}$-alkoxy or $CF_3$ groups, or benzyl, which is unsubstituted or substituted by 1, 2 or 3 fluorine, chlorine or bromine atoms or $C_{1-5}$-alkyl, $C_{1-5}$-alkoxy or $CF_3$ groups, or
- $R^4$ and $R^5$ taken together form a $(CH_2)_4$, $(CH_2)_5$, $(CH_2)_6$ or $CH_2CH_2OCH_2CH_2$ radical, or $NR^4R^5$ is the radical of an amino acid or peptide, wherein the carboxyl group and any other functional group present is unprotected or protected by a protective group, which comprises reacting an acid of the formula II

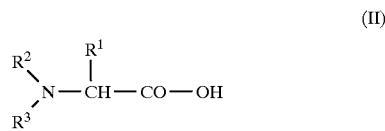
(II)

with a primary or secondary amine of the formula

in the presence of an alkanephosphonic acid anhydride.

2. The process defined in claim 1, wherein the primary or secondary amine is an amino acid, an amino acid ester or an amino acid amide or a peptide.

3. The process defined in claim 1, wherein the alkanephosphonic anhydride is n-propanephosphonic anhydride.

4. The process defined in claim 1, wherein the α-dialkylamino carboxylic acid is an N,N-dimethyl- or N-benzyl-N-methylamino carboxylic acid.

5. The process defined in claim 1, wherein the α-dialkylamino carboxylic acid is N,N-dimethylvaline, N,N-dimethylisoleucine, N-benzyl-N-methylvlaine or N-benzyl-N-methylisoleucine.

* * * * *